US00PP27857P2

(12) United States Plant Patent
Probst

(10) Patent No.: US PP27,857 P2
(45) Date of Patent: Apr. 4, 2017

(54) ***COREOPSIS* PLANT NAMED 'ENCHANTED EVE'**

(50) Latin Name: ***Coreopsis* hybrid**
Varietal Denomination: Enchanted Eve

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 92 days.

(21) Appl. No.: 14/545,030

(22) Filed: Mar. 18, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

American Nurseryman 2015 Dec. 2014, retrieved on Aug. 4, 2016, retrieved from the Internet at <http://www.amerinursery.com/content/AN/pdf/2015_AN_NewPlants.pdf> pp. 4 and 36.*

Emerald Coast Grower Starter Plants 2014-2015 catalog, pp. 1-3, 8-9 and 26-27.*

Pioneer Gardens, Inc. 2014-2015 Program and Availability, retrieved on Aug. 18, 2016, retrieved from the Internet at <https://nebula.wsimg.com/a8e14aaf5f2c1ab73574f0980ec0bb03?AccessKeyId=D4DC3ED90C9EAD58C2B4&disposition=0&allow origin=1> Aug. 27, 2014, pp. 1-20.*

* cited by examiner

*Primary Examiner* — June Hwu

(74) *Attorney, Agent, or Firm* — Penny J. Aguirre

(57) ABSTRACT

A new cultivar of hybrid *Coreopsis* named 'Enchanted Eve' that is characterized by its compact plant habit reaching an average of 23 cm in height and 50 cm in width, its nearly sterile florets result in a floriferous and long bloom season that does not require deadheading with bloom commencing in late-June and lasting until frost in Connecticut, its large inflorescences with ray florets that are light yellow in color with a two-toned red eye that expands to cover nearly the entire surface of the ray florets in cooler temperatures, its cold hardiness at least to U.S.D.A. Zone 5a, and its resistance to powdery mildew and leafspot.

2 Drawing Sheets

Botanical classification: *Coreopsis* hybrid.
Variety denomination: 'Enchanted Eve'.

BACKGROUND OF THE INVENTION

The present invention relates to a new and distinct cultivar of *Coreopsis* plant, botanically of hybrid origin and known as *Coreopsis* 'Enchanted Eve' and will be referred to hereinafter by its cultivar name, 'Enchanted Eve'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars in a wide range of flower colors and plant forms that have sturdy plant habits, exhibit a true perennial habit, and are cold hardy to at least U.S.D.A Zone 5a.

The new cultivar arose from a cross made by the Inventor in August of 2010 in his test garden in Hubbardston, Mass. between an unnamed, proprietary plant in the Inventor's breeding program, reference no. T 08-1 (not patented), as the female parent and pollen that was pooled from a variety of unnamed, proprietary plants (not patented) from his breeding program as the male parent (all nearly sterile). The exact male parentage is therefore unknown. 'Enchanted Eve' was selected in September 2011 as a single unique plant amongst the resulting seedlings.

Asexual reproduction of the new cultivar was first accomplished by stem cuttings under the direction of the Inventor in Kensington, Conn. in September of 2011. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Enchanted Eve' as a new and distinct cultivar of *Coreopsis*.

1. 'Enchanted Eve' exhibits a compact plant habit reaching an average of 23 cm in height and 50 cm in width.
2. 'Enchanted Eve' is nearly sterile and exhibits a floriferous and long bloom season that does not require deadheading, blooming commences in late-June and lasts until frost in Kensington, Conn.
3. 'Enchanted Eve' exhibits large inflorescences with ray florets that are light yellow in color with a suffused two-toned red eye that expands to cover nearly the entire surface of the ray florets in cooler temperatures.
4. 'Enchanted Eve' exhibits cold hardiness at least to U.S.D.A. Zone 5a.
5. 'Enchanted Eve' exhibits resistance to powdery mildew and leafspot.

The female parent differs from 'Enchanted Eve' in having larger inflorescences with ray florets that are white in color with a very small burgundy colored eye and in having a taller plant height. 'Enchanted Eve' can be most closely compared to the *Coreopsis* cultivars 'Cosmic Eye' (U.S. Plant Pat. No. 22,601) and 'Little Sundial' (U.S. Plant Pat. No. 18,460). 'Cosmic Eye' is similar to 'Enchanted Eve' in having a compact plant habit, in having large inflorescences, and in having a long bloom season that does not require deadheading. 'Cosmic Eye' differs from 'Enchanted Eve' in having inflorescences with ray florets that are bright yellow in color with a large and well-defined burgundy colored eye, and in being more difficult to propagate after flowering commences. 'Little Sundial' is similar to 'Enchanted Eve' in having a compact plant habit. 'Little Sundial' differs from 'Enchanted Eve' in having a bun-shaped plant habit that is smaller in width (fills the pot less quickly) and in having inflorescences with ray florets that are gold in color with a very small red colored blotch at the base (single color).

BRIEF DESCRIPTION OF THE DRAWINGS

The accompanying colored photographs illustrate the overall appearance and distinct characteristics of the new *Coreopsis*. The photograph in FIG. 1 was taken of five month-old plants of 'Enchanted Eve' as grown in outdoors in the ground in New Braintree, Mass. The photographs in FIG. 2 and FIG. 3 were taken of a three month-old plant (from a 128-cell plug) of 'Enchanted Eve' as grown outdoors in a one-gallon container in Kensington, Conn.

The photograph in FIG. 1 provides a top view of two plants of 'Enchanted Eve' in bloom during cooler temperatures (with red coloration expanded on ray florets).

Figure 1:
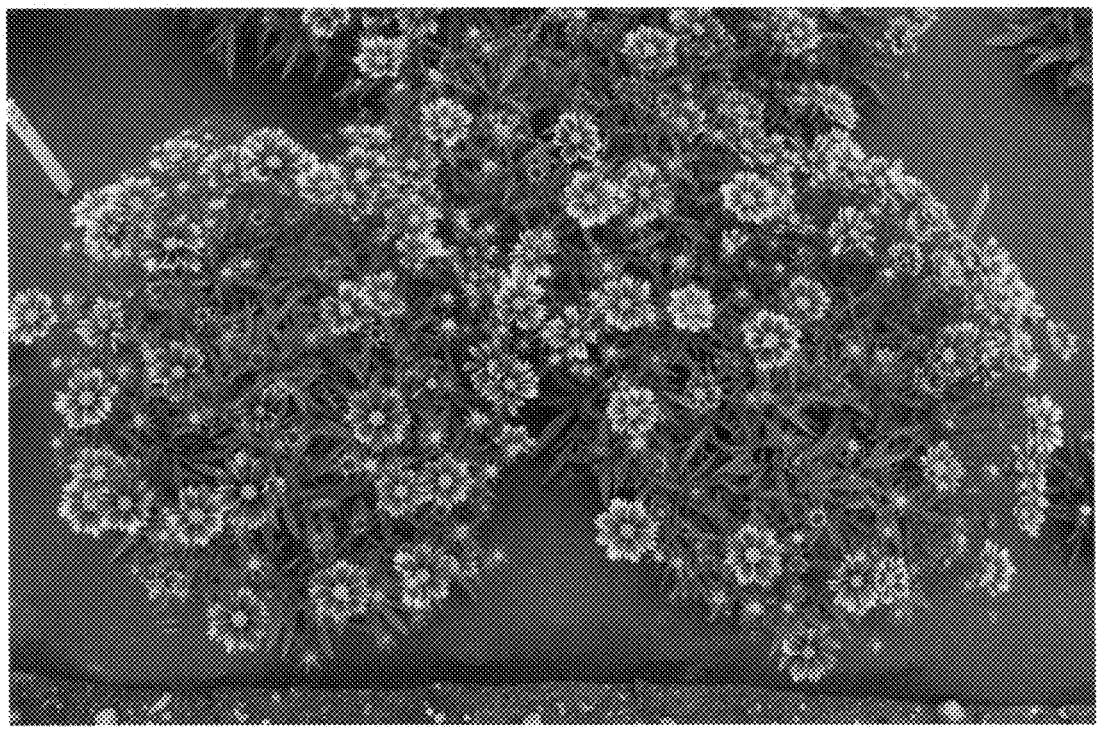
Figure 2:
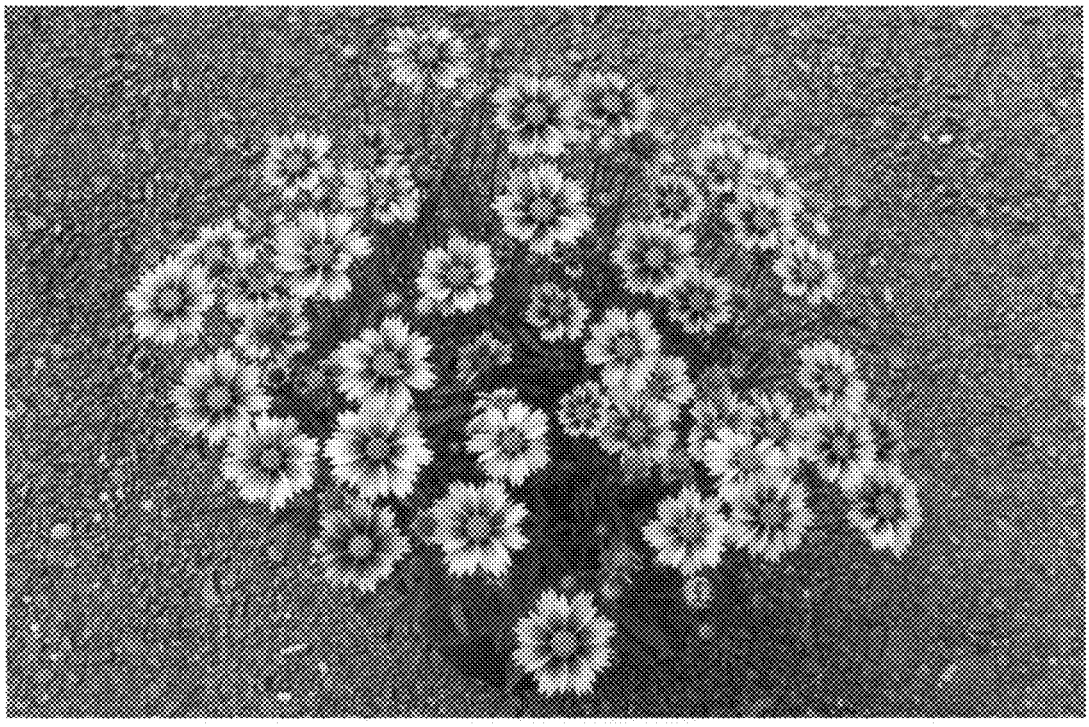

The photograph in FIG. 2 provides a view of 'Enchanted Eve' in bloom as grown during warmer temperatures.

Figure 3:
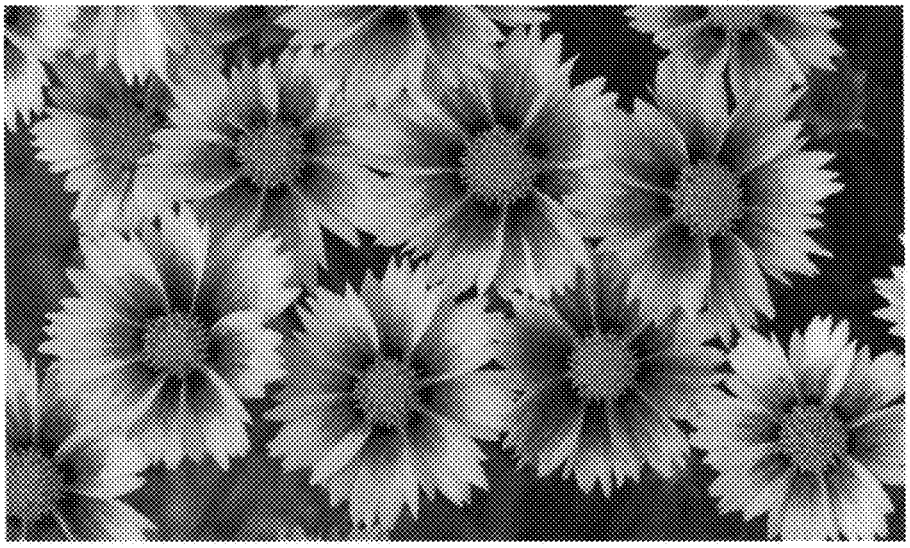

The photograph in FIG. 3 provides a close-up view of the inflorescences of 'Enchanted Eve' as grown during warmer temperatures.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of plants of the new cultivar that are three months in age (from a 128-cell plug) as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from late-June until frost in Kensington, Conn.

*Plant type.*—Herbaceous perennial.

*Plant habit.*—Compact, clump-forming, and densely branched.

*Height and spread.*—An average of 23 cm in height and 50 cm in width.

*Cold hardiness.*—At least in U.S.D.A Zone 5a.

*Diseases resistance.*—Has been observed to be highly resistant to powdery mildew caused by *Podosphaera macularis* and leafspot by *Pseudomonas cichorii.*

*Root description.*—Fibrous when young, becoming more fleshy with age.

*Propagation.*—Stem cuttings.

*Growth rate.*—Vigorous, but stays compact, quickly fills out a one-gallon container.

Stem description:

*Shape.*—Oval, ridged.

*Stem color.*—Young stems; 146C, mature stems; 146C with marking of 187A near the nodes, oldest part of the stem is bark-like and a blend of N199B and 199A.

*Stem size*—Main stems; an average of 5 cm in length (excluding terminal peduncle) and 2 mm in width, secondary; average of 4 cm in length and 2 mm in width (excluding peduncles).

*Stem surface.*—Young stems; glabrous, mature stems; ridged and bark like.

*Stem aspect.*—Nearly vertical.

*Branching habit.*—An average of 8 main branches, up to 4 secondary branches per main stem.

*Internode length.*—An average of 2 cm.

Foliage description:

*Leaf division.*—Simple.

*Leaf margins.*—Entire to deeply tri-fid (almost leaflet-like).

*Leaf size.*—Variable, up to 4 cm in length and 2 cm in width when tri-fid, up to 4 cm in length and 6 mm in width when entire.

*Leaf shape.*—Lanceolate when entire, lanceolate lobes when tri-fid.

*Leaf base.*—Truncate to stem.

*Leaf apex.*—Acute.

*Leaf venation.*—Pinnate, not prominent, matches leaf color on upper and lower surface.

*Leaf attachment.*—Sessile.

*Leaf arrangement.*—Opposite.

*Leaf surface.*—Glabrous on upper and lower surface.

*Leaf color.*—Young and mature upper surface; 146A, young and mature lower surface; 146B.

Inflorescence description:

*Inflorescence type.*—Composite with a single row of ray florets surrounding disk florets in the center, forming a radiant head, inflorescences are borne on branch terminals in loose corymbs.

*Lastingness of inflorescence.*—8 to 10 days until senescence of ray florets, longer in cool temperatures, bracts and disk florets are persistent.

*Fragrance.*—Faint fragrance.

*Quantity of inflorescences.*—An average of 10 composite inflorescences per corymb and one corymb per main branch.

*Inflorescence size.*—Corymbs; an average of 8 cm in width and 11 cm in height, composite; an average of 1 cm in depth and up to 6 cm in diameter with disk portion an average of 1.4 cm in diameter.

*Inflorescence buds.*—An average of 6 mm in depth and in diameter, spherical in shape, color; top 151A blend with 7A in mid-section, base 144A.

*Peduncle.*—An average of 9 cm in length and 1 mm in width, glabrous surface, 144A in color.

Involucral bracts:

*Bract number.*—Two rows of 8.

*Bract arrangement.*—Outer bracts are un-fused and reflexed when flower is fully open and becoming horizontal after ray florets drop, inner bracts are 50% fused and surround receptacle with a campanulate form with apical portion un-fused, spreading, and held close to lower surface of ray florets. 50% is fused at base, free portion is spreading outward and reflexed when flower is fully open, held horizontal after florets have dropped.

*Bract size.*—Outer bracts; an average of 1 cm in length and 4 mm in width, inner bracts 6 mm in length and 2 mm in width.

*Bract color.*—Outer bracts; translucent and N144A with base 146B, inner bracts 144A, with apex 147A and translucent edges.

*Bract texture.*—Glabrous on both surfaces.

*Bract apex.*—Acute.

*Bract base.*—Truncate.

*Bract margins.*—Entire.

*Bract shape.*—Broadly lanceolate.

Ray florets (sterile):

*Number.*—An average of 8 arranged primarily in one row.

*Shape.*—Ovate.

*Size.*—An average of 2.3 cm in length and 1.5 cm in width.

*Apex.*—4 notched.

*Base.*—Broadly cuneate.

*Margins.*—Entire with apex notched.

*Aspect.*—Held horizontal to slightly downward.

*Texture.*—Glabrous on inner and outer surfaces.

*Color.*—Opening and fully open upper surfaces; 7A with a slight overlay of 15A on the edges and margins, heavily suffused with 183B at the base fading to a blend between 45C and 182A to 182B towards the apex in cooler temperatures and heavily suffused with 183B at the base fading to a moderate suffusion with a blend between 45C and 182A to 182B towards the basal-mid section further fading to a light suffusion with 182B in the apical-mid section in warmer temperatures, opening and fully open lower surfaces; 12A.

Disk florets (perfect):

*Shape.*—Tubular, corolla is fused, flared at apex.

*Number.*—An average of 100.

*Size.*—About 4 mm in length and 1 mm in width.

*Color.*—En masse; 21A, corolla; base of tube is 11B in color, flared portion is 17A and translucent.

*Receptacle.*—About 7 mm in diameter and 3 mm in depth, 145C in color.

Reproductive organs:

*Presence.*—Disk florets are perfect, ray florets are sterile.

*Gynoecium.*—1 Pistil, 4 mm in length, style is very fine and about 13A in color and translucent, bifid pilose stigma is 21A in color with branches about 1 mm in length and recurved, ovary is 3 mm in length, 1 mm in width, inferior, and 5C in color.

*Androcoecium.*—5 stamens, fused into tube surrounding style, 2 mm in length and 0.5 mm in width, about 166A in color, no pollen observed.

*Fruit/seed.*—No fruit or seed development was observed, plants have been observed to be nearly sterile.

It is claimed:

1. A new and distinct cultivar of *Coreopsis* plant named 'Enchanted Eve' as herein illustrated and described.

* * * * *